(12) United States Patent
Sambanthmurthi et al.

(10) Patent No.: US 8,557,309 B2
(45) Date of Patent: Oct. 15, 2013

(54) ANTIMICROBIAL COMPOSITION BASED ON BOTANICAL EXTRACTS FROM OIL PALM VEGETATION LIQUOR

(71) Applicant: Malaysian Palm Oil Board, Selangor (MY)

(72) Inventors: Ravigadevi Sambanthmurthi, Selangor Darul Ehsan (MY); Yew Ai Tan, Kuala Lumpur (MY)

(73) Assignee: Malaysian Palm Oil Board, Selangor (MY)

( * ) Notice: Subject to any disclaimer, the term of this patent is extended or adjusted under 35 U.S.C. 154(b) by 0 days.

(21) Appl. No.: 13/648,185

(22) Filed: Oct. 9, 2012

(65) Prior Publication Data

US 2013/0035299 A1 Feb. 7, 2013

Related U.S. Application Data

(62) Division of application No. 12/746,506, filed as application No. PCT/MY2008/000177 on Dec. 5, 2008, now abandoned.

(30) Foreign Application Priority Data

Dec. 7, 2007 (MY) .............................. PI 20072189

(51) Int. Cl.
*A61K 36/00* (2006.01)
(52) U.S. Cl.
USPC ........................................ 424/725

(58) Field of Classification Search
None
See application file for complete search history.

(56) References Cited

U.S. PATENT DOCUMENTS

| 5,981,587 A | 11/1999 | Guzman-Harty et al. |
| 2003/0031740 A1 | 2/2003 | Sambanthamurthi et al. |

FOREIGN PATENT DOCUMENTS

| EP | 1837409 A1 * | 9/2007 |
| JP | 06-157229 | 6/1994 |
| WO | WO 02/081724 A1 * | 10/2002 |
| WO | WO-2008/127085 | 10/2008 |

OTHER PUBLICATIONS

Balasundram, et al., "Antioxidant properties of palm fruit extracts," Asia Pacific Journal of Clinical Nutrition,(2005), 4(4):319-324.
International Search Report dated Jul. 27, 2009 for PCT Application No. PCT/MY2008/000177.

* cited by examiner

*Primary Examiner* — Qiuwen Mi
(74) *Attorney, Agent, or Firm* — Foley & Lardner LLP

(57) ABSTRACT

The present invention provides an antimicrobial composition comprising compounds extracted from the vegetation liquor of the palm oil milling process has been suggested. This composition is rich in antioxidants and exhibits enhanced antimicrobial activity and bactericidal effect against a number of micro-organisms.

6 Claims, No Drawings

ANTIMICROBIAL COMPOSITION BASED ON BOTANICAL EXTRACTS FROM OIL PALM VEGETATION LIQUOR

RELATED PATENT APPLICATIONS

This application is a divisional of U.S. application Ser. No. 12/746,506 filed Aug. 20, 2010, which is a U.S. National Phase of PCT Application No. PCT/MY2008/000177 filed on Dec. 5, 2008, which claims priority from Malaysian Patent Application No. PI 20072189, filed Dec. 7, 2007, each of which are incorporated herein by reference in their entirety.

FIELD OF INVENTION

The present invention relates to compositions having antimicrobial properties and comprises compounds extracted from plant material. More particularly, the present invention relates to a composition comprising botanical extracts containing phenolic compounds from vegetation liquor of oil palm for a wide scope of antimicrobial applications.

BACKGROUND OF INVENTION

In the health industry of the emergent world, bacterial related diseases and infections which are recognized or identified are mostly therapeutically prevailed by way of antibiotics and bacteriostatic agents. Accordingly, there is a great momentum in producing modern microbial antibiotics and medicaments globally. Nonetheless, such modern antibiotics and medicaments may represent a considerable number of complications including prohibitively expensive in terms of its sources and increasing toxic effects. Owing to this eminent circumstance, substantial progress, has been made in this regard in order to further determine and thus provide a natural origin solution to economically produce such antibiotics or bacteriostatic based treatments.

Proceeding from the above, one of the natural origin solutions is discovered in plants, whereby the usage of phenolics and flavanoids, which are most abundant and ubiquitous products of secondary plant metabolism, has been recently implicated therapeutically. Under normal condition, they are often used as a defense mechanism against animal predation and the like.

Plants which are used for medicinal studies contain a wide range of substances and compounds that can be used to treat chronic as well as infectious diseases. Such implication is increasing rapidly, more particularly in areas where the use of plant based medicines is of great importance.

Additionally, recent studies have begun to examine and heightened the role of plants extract in the context of producing treatments or medications against microbial diseases. Further studies on the extracts and biologically active compounds isolated from plants have significantly increased in the past decades.

A relatively conventional exemplary of a plant species which is found to be exhibiting considerable antimicrobial effect is the sesame leaves (Shittu 2006). Studies were conducted based on the leaves of the said plant species (*Sesame radiatum*) for antimicrobial activity, and the ethanolic extract of said plant has shown mild inhibitory effect on the growth of *streptococcus pneumoniae* and *candida albicans*. The said ethanolic extract contained essential oils, mainly phenolic and carboxylic acids groups.

The present invention focuses on the enhancement of the medicinal properties of another prominent plant species, namely the palm fruit (*Elaies guineensis*). It is presently known in the art that the palm fruit botanical extract contains a rich source of phenolic compounds, beta-carotene and vitamin E, which are prominent nutritional antioxidants that act as scavengers of oxygen atom or free radicals, and thus known to be effective against skin aging, heart disease and cancer.

In addition, the palm fruit is the source of palm oil which is obtained from palm fruit and palm kernel oil, whereby the source is the fruit seeds. According to studies, palm oil and palm kernel oil are composed of about 50% and 80% of fatty acids, respectively. The palm fruit contains fatty acids ranging from $C_6$ to $C_{18}$, at which the palm oil is found to contain high amount of palmitic acid while the palm kernel oil is found to contain high amount of lauric acid. In addition to the phenolic compounds, Vitamin E and beta-carotene, the high content of fatty acids in palm fruit may also play a significant role in providing the bacteriostatic effect on certain and antimicrobial activity on certain micro-organisms.

Apart from the above, high content of phenolics may contribute significantly to bactericidal properties in palm fruit based extract.

The present invention provides a new approach in using palm fruit, particularly in preparing a composition based on botanical extracts obtained from oil palm vegetation liquor for providing bacteriostatic or inhibitory effect against a number of micro-organisms.

It is further added that the high content of phenolics in the composition in accordance with the present invention provides bactericidal effect against micro-organisms.

Consequently, the primary object of the present invention to provide a composition based on compounds extracted from vegetation liquor of the palm oil milling process where the composition exhibits inhibitory effect against micro-organisms.

It is a further object of the present invention to provide an improved composition and method based on compounds extracted from vegetation liquor of the palm oil milling process for producing a broad spectrum antimicrobial effect which is non-toxic.

It is further the object of the present invention to provide an improved composition and formulation for producing a composition containing antioxidants and phenolics obtained from the botanical extracts of oil palm vegetation liquor devoid of chemically prepared adverse drug reactions in a patient in need thereof.

It is a further object of the present invention to provide a composition and formulation for producing a composition containing compounds obtained from the botanical extracts oil palm vegetation liquor having antimicrobial or bacteriostatic effect.

It is a further object of the present invention to provide a composition and formulation for producing a composition containing compounds obtained from the botanical extracts oil palm vegetation liquor having bactericidal effect against micro-organisms due to the high content of phenolics in the said composition.

SUMMARY OF INVENTION

The present invention discloses an antimicrobial composition comprising compounds extracted from the vegetation liquor of the palm oil milling process.

DETAILED DESCRIPTION OF THE INVENTION

Further understanding of the object, construction, characteristics and functions of the invention, a detailed description with reference to the embodiments is given in the following.

The inventors of the present invention discovered that the composition prepared from the extract of oil palm vegetation exhibits enhanced antimicrobial activity.

It is therefore purpose of this invention is to present composition containing extract of oil palm vegetation liquor from the oil palm milling process for antimicrobial applications, in particular for treatments of bacterial related diseases and infections.

The composition of the present invention may prevent/inhibit the growth of micro-organism(s). This may include slowing or arresting a micro-organism, such as bacteria or by eliminating the said micro-organism(s) present on contact with the composition of the present invention.

It is noted that it would be advantageous for the composition of the present invention to be bactericidal or bacteriostatic effective against gram positive and gram negative bacteria.

Accordingly, the present invention also relates to an extraction process of antioxidants from the oil palm vegetation liquor from the milling process. The processing of oil palm produces larger amounts of vegetation liquor rich in phenolic compounds, fruit acids, fruit sugars and glycerol which can be further enriched using conventional membrane filtration technology.

It is noted that extracts derived from the vegetation liquor of oil palm, wherein the major constituents are phenolics, fruit acids, fruit sugars and glycerol have properties that exhibit antimicrobial activity and bactericidal effect against certain micro-organisms.

BEST MODE FOR CARRYING OUT THE INVENTION

Materials and Methods

Extract Materials

The preparation of the composition of the present invention is described in detail by referring to the experimental examples. However, the present invention is not limited to these examples.

Accordingly, the present invention also relates to an extraction process of antioxidants from the oil palm vegetation liquor from the milling process. The processing of oil palm produces larger amounts of vegetation liquor rich in phenolic compounds, fruit acids, fruit sugars and glycerol which can be further enriched using conventional membrane filtration technology.

For the experimental examples, inventors isolated botanical extracts comprising phenolic compounds, fruit acids, fruit sugars and glycerol from oil palm vegetation liquor from the palm oil milling process and the prepared formulations containing these extracts.

Preparation of Extracts

Unless otherwise specified, throughout the following examples, the oil palm phenolic extract employed is a crude solvent-free extract.

The present invention focuses on antimicrobial compositions comprising of high content of phenolic compounds which is discovered to exhibit antimicrobial and bactericidal properties.

The biologically active extracts of palm vegetation liquor useful in this invention can be prepared by any means capable of extracting phenolic compounds from the vegetation liquor using standard extraction techniques or techniques well known in the art. Such extractions include but are not limited to ethanol, methanol, acetone, ethyl acetate and butanol.

In addition to direct use of an extract, it is also possible to use different fractions of the oil palm phenolic compounds. What constitutes an effective amount of an extract, or an active portion thereof, will depend on the purity of the extract. For example, if a crude phenolic-containing extract of about 10% purity is employed, the extract will normally be used at a concentration range of about 0.01-20% by weight of the composition. At a higher level of purity, a smaller percentage will be required to achieve the same effect. Assuming a substantially pure phenolic extract, i.e. an extract containing at least 80% active phenolics, the level will be about 0.01 to about 8% by weight of the composition.

Antimicrobial Screening

One of the conventional steps which may be employed in regards to the antimicrobial screening methodology is agar-well diffusion method of the modified Collins et. al (1995) whereby the antimicrobial activity of the composition of the present invention against a number of micro-organisms is accordingly tested.

It should be noted that other suitable conventional methodologies may also be selected for the purpose of the antimicrobial screening.

Antimicrobial Activity

The antimicrobial activity may be employed based on the conventional disc or paper diffusion method. In the disc diffusion method, different concentrations of extracts are loaded on the sterile disc, and subsequently placed on the surface of the medium as prepared. The plates are prepared with the suitable media, poured into petri plates. Subsequently, the said plates are allowed to solidify and a predetermined amount of innoculum suspension is swabbed uniformly across the plates and allowed to dry within a predetermined period. In the next step, the loaded disc accordingly positioned on the surface of the medium and allowed to diffuse within a predetermined period of time. The plates are therefore kept for incubation at a suitable temperature and period of time. Upon completion of incubation, the inhibition zones are formed around the disc and thus measured. The results indicate that the extract performed inhibitory activity against the tested micro-organisms. This experiment may be performed in triplicate.

It should be noted that other suitable conventional methodologies may also be selected for the purpose of the antimicrobial activity.

Application(s)

The antimicrobial composition in accordance with the present invention may be used for a wide range of applications.

In one aspect it is understood by a person skill in the art that the composition of the present invention may be used in pure form or in combination with additional components which preferably do not materially affect the properties of the composition.

In another aspect, the composition may be incorporated in pharmaceutical formulations for treatment of one or more diseases or infections.

In a further aspect, the composition may be used for personal hygiene or cosmoceutical applications.

Although the present invention has been described with reference to the preferred embodiments and examples thereof, it is apparent to those skilled in the art that a variety of modifications and changes may be made without departing from the scope of the present invention which is intended to be defined by the appended claims.

The invention claimed is:

1. A method for treating a subject with a bacterial infection, the method comprising administering a therapeutically effective amount of a composition comprising extract from the vegetation liquor of the palm oil milling process to a subject in need thereof.

2. The method of claim 1, wherein the composition comprises phenolic compounds, fruit acids, fruit sugars and glycerol.

3. The method of claim 1, wherein the composition is formulated in a pharmaceutically acceptable carrier.

4. A method for inhibiting growth of bacteria on a surface, the method comprising contacting said surface with a composition comprising compounds extracted from the vegetation liquor of the palm oil milling process.

5. The method of claim 4, wherein the composition comprises phenolic compounds, fruit acids, fruit sugars and glycerol.

6. The method of claim 4, wherein the composition is formulated in a pharmaceutically acceptable carrier.

\* \* \* \* \*